United States Patent
Han et al.

(10) Patent No.: US 12,248,013 B2
(45) Date of Patent: Mar. 11, 2025

(54) SYSTEM-LEVEL MALFUNCTION INDICATOR IN AUTONOMOUS VEHICLES

(71) Applicant: TUSIMPLE, INC., San Diego, CA (US)

(72) Inventors: Xiaoling Han, San Diego, CA (US); Yu-Ju Hsu, Tucson, AZ (US)

(73) Assignee: TUSIMPLE, INC., San Diego, CA (US)

( * ) Notice: Subject to any disclaimer, the term of this patent is extended or adjusted under 35 U.S.C. 154(b) by 0 days.

(21) Appl. No.: 18/348,589

(22) Filed: Jul. 7, 2023

(65) Prior Publication Data
US 2023/0349963 A1 Nov. 2, 2023

Related U.S. Application Data

(63) Continuation of application No. 16/727,829, filed on Dec. 26, 2019, now Pat. No. 11,726,124.

(51) Int. Cl.
*G01R 31/00* (2006.01)
*B60T 17/22* (2006.01)
(Continued)

(52) U.S. Cl.
CPC .......... *G01R 31/007* (2013.01); *B60T 17/221* (2013.01); *F01N 11/00* (2013.01);
(Continued)

(58) Field of Classification Search
CPC ......... B60R 16/00; B60R 16/02; B60T 17/00; B60T 17/18; B60T 17/22; B60T 17/221; B60W 2050/0215; B60W 2050/022; B60W 50/00; B60W 50/02; B60W 50/0205; B60W 50/04; B60W 50/045; B60W 60/00;
(Continued)

(56) References Cited

U.S. PATENT DOCUMENTS 6,502,025 B1 * 12/2002 Kempen ............ B62D 15/0215
701/41
2004/0162650 A1 8/2004 Kueperkoch
(Continued)

FOREIGN PATENT DOCUMENTS

CN 108880590 A 11/2018
CN 109709963 A 5/2019
(Continued)

OTHER PUBLICATIONS

Nielles, Daniel. European Patent Application No. 20215438, Extended European Search Report Mailed Jun. 1, 2021 (pp. 1-7).
(Continued)

*Primary Examiner* — Charles J Han
(74) *Attorney, Agent, or Firm* — Perkins Coie LLP

(57) ABSTRACT

Devices, systems and methods for using system-level malfunction indicators to monitor the operation and resiliency of the autonomous driving system components are described. One example of a method for diagnosing a fault in a component of an autonomous vehicle includes receiving, from an electrical sub-component of the component, an electrical signal, receiving, from an electronic sub-component of the component, a message, and determining, based on the electrical signal and the message, an operational status of the component.

15 Claims, 5 Drawing Sheets

(51) Int. Cl.
  *F01N 11/00* (2006.01)
  *F02M 63/00* (2006.01)
  *G01K 15/00* (2006.01)
  *G01N 33/00* (2006.01)
  *G01P 21/02* (2006.01)

(52) U.S. Cl.
  CPC ....... *F02M 63/0015* (2013.01); *G01K 15/007* (2013.01); *G01N 33/007* (2013.01); *G01P 21/02* (2013.01)

(58) Field of Classification Search
  CPC ........... B60W 60/001; B60W 60/0025; B60W 60/00259; F01N 11/00; F02M 63/00; F02M 63/0012; F02M 63/0014; F02M 63/0015; G01K 15/00; G01K 15/007; G01N 33/00; G01N 33/0004; G01N 33/0009; G01N 33/007; G01P 21/00; G01P 21/02; G01R 31/00; G01R 31/005; G01R 31/006
  See application file for complete search history.

(56) References Cited

U.S. PATENT DOCUMENTS

| | | |
|---|---|---|
| 2016/0144866 A1 | 5/2016 | Seo |
| 2017/0066442 A1 | 3/2017 | Woodley |
| 2018/0187583 A1 | 7/2018 | De |
| 2019/0210613 A1* | 7/2019 | Sun ........................ G05B 23/00 |
| 2020/0086884 A1* | 3/2020 | Wang .................. B60W 30/181 |
| 2021/0199705 A1 | 7/2021 | Han et al. |

FOREIGN PATENT DOCUMENTS

| | | |
|---|---|---|
| CN | 110254439 A | 9/2019 |
| WO | 2019140277 A2 | 7/2019 |

OTHER PUBLICATIONS

European Patent Office, Extended European Search Report for EP Appl. No. 24195248.0, mailed on Dec. 9, 2024, 7 pages.

* cited by examiner

SYSTEM-LEVEL MALFUNCTION INDICATOR IN AUTONOMOUS VEHICLES

CROSS-REFERENCE TO RELATED APPLICATIONS

This patent document is a continuation of U.S. patent application Ser. No. 16/727,829, filed on Dec. 26, 2019. The aforementioned application of which is incorporated herein by reference in their entireties.

TECHNICAL FIELD

This document generally relates to lighting control to improve autonomous vehicular driving.

BACKGROUND

Autonomous vehicle navigation is a technology for sensing the position and movement of a vehicle and, based on the sensing, autonomously controlling the vehicle to navigate towards a destination. Autonomous vehicle navigation can have important applications in transportation of people, goods and services. One of the components of autonomous driving, which ensures the safety of the vehicle and its passengers, as well as people and property in the vicinity of the vehicle, is the use of a system-level malfunction indicator to monitor the operation and resiliency of the autonomous driving system components.

SUMMARY

Disclosed are devices, systems and methods for system-level malfunction indicators to monitor the operation and resiliency of the autonomous driving system components. In one aspect, the disclosed technology uses system-level malfunction indicator to monitor the operation and resiliency of the autonomous driving system components. This method includes receiving, from an electrical sub-component of the component, an electrical signal; receiving, from an electronic sub-component of the component, a message; and determining, based on the electrical signal and the message, an operational status of the component.

In another aspect, the above-described method is embodied in the form of processor-executable code and stored in a computer-readable program medium.

In yet another aspect, a device that is configured or operable to perform the above-described method is disclosed. The device may include a processor that is programmed to implement this method.

The above and other aspects and features of the disclosed technology are described in greater detail in the drawings, the description and the claims.

DETAILED DESCRIPTION

The transportation industry has been undergoing considerable changes in the way technology is used to control the operation of the vehicles. As exemplified in the automotive passenger vehicle, there has been a general advancement towards shifting more of the operational and navigational decision making away from the human driving and into on-board computing power. This is exemplified in the extreme by the numerous under-development autonomous vehicles. Current implementations are in intermediate stages, such as the partially-autonomous operation in some vehicles (e.g., autonomous acceleration and navigation, but with the requirement of a present and attentive driver), the safety-protecting operation of some vehicles (e.g., maintaining a safe following distance and automatic braking), the safety-protecting warnings of some vehicles (e.g., blind-spot indicators in side-view minors and proximity sensors), as well as ease-of-use operations (e.g., autonomous parallel parking).

Vehicles operated with any level of autonomy rely on their components working reliably, which requires monitoring the operation of the components. In some embodiments, both the electrical and electronic sub-components of a component may be monitored to ensure that the component is operating as intended. If the operational status of a component is designated as faulty, alternate components or measures can be harness to continue autonomous operation.

Section headings are used in the present document to improve readability of the description and do not in any way limit the discussion or the embodiments (and/or implementations) to the respective sections only.

Examples of System-Level Malfunction Indicators

Figure 1:
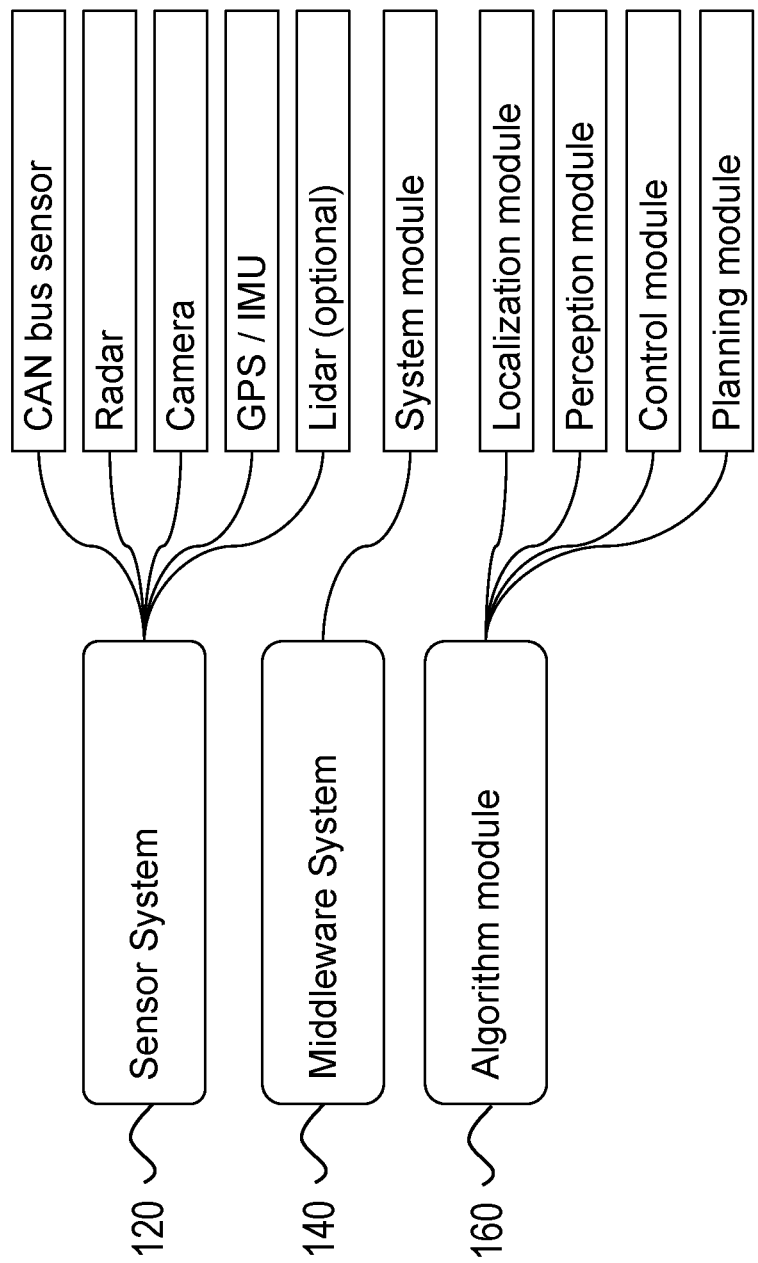
FIG. 1 shows a block diagram of example components of an autonomous vehicle.

FIG. 1 shows a block diagram of example components of a vehicle that can support remote safe driving. In some embodiments, the vehicle may include a sensor system 120, a middleware system 140, and an algorithm module 160. In some embodiments, one or more of these components may be part of an electronic control unit (ECU) system (not shown in FIG. 1). In other embodiments, the ECU system may control one or more of these systems and modules.

In an example, the sensor system 120 may include a CAN bus sensor, a camera, radar capabilities, a GPS unit and/or an IMU, and Lidar capabilities. In another example, the middleware system 140 may include the system module, and the algorithm module 160 may include a localization module, a perception module, a control module, and a planning module.

In some embodiments, one or more of the components shown in FIG. 1 include both electrical and electronic components, both of which need to be monitored to ensure the reliable operation of the component. For an example, there may be electrical glitches (e.g., voltage spikes or inrush currents) that can adversely affect the component. For another example, the component may determine that it has reached an unintended state (e.g., due to an erroneous input or output) and generates an error message indicative of this state.

Figure 2:
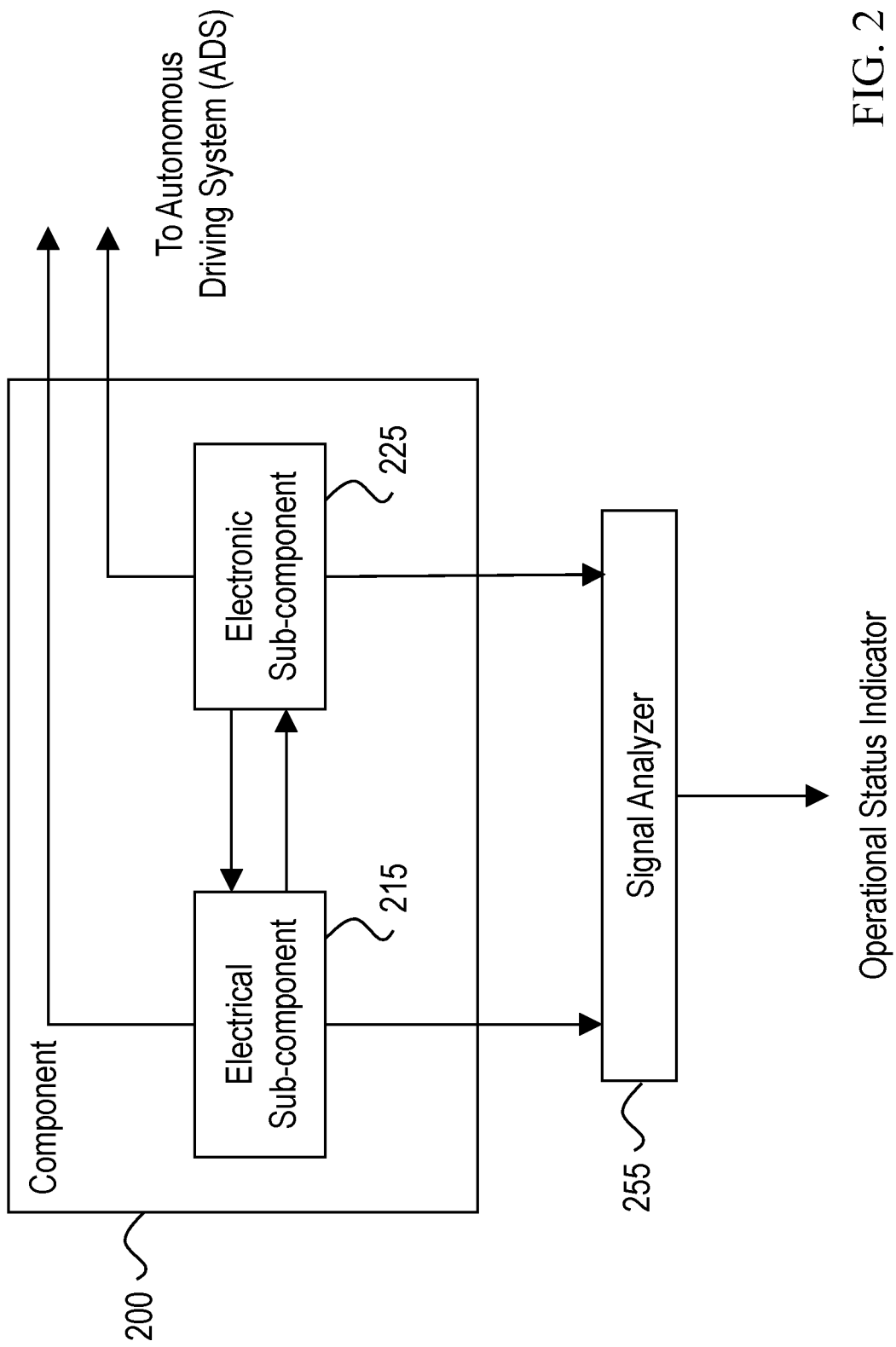
FIG. 2 shows a block diagram of an example component with electrical and electronic sub-components, in accordance with embodiments of the disclosed technology.

FIG. 2 shows a block diagram of an example component with electrical and electronic sub-components. As shown therein, a component 200 may include an electrical sub-component 215 and an electronic sub-component 225, which can interact to ensure the intended operation of the component. In addition to sending signals and messages to the autonomous driving system (ADS), the electrical and electronic sub-components (215 and 225, respectively) send the same signals and messages to a signal analyzer 255. In some embodiments, the signal analyzer 255 can be configured to process the signals and messages and generate an operational status indicator.

In some embodiments, the messages generates by one or more components (of the autonomous driving system itself) include a vehicle status message, which may be defined as including the following subfields, one or more of which may be transmitted at each time:

(1) vehicle running status as a 1-bit field with a "0" indicating that the vehicle is running and a "1" indicating that the vehicle has stopped;

(2) vehicle self-status using the standard or extended frame formats (as described in Controller Area Network (CAN) 2.0 A and CAN 2.0 B);

(3) hardware status defined as:

| Field name | Length (bits) | Purpose |
| --- | --- | --- |
| Mainboard status | 6 | Indicates status of mainboard |
| CPU status | 6 | Indicates status of CPU |
| Memory status | 6 | Indicates status of memory |
| GPU status | 10 | Indicates status of GPU |
| Power status | 6 | Indicates status of power supply |

(4) system status defined as:

| Field name | Length (bits) | Purpose |
| --- | --- | --- |
| Middleware module status | 10 | Indicates status of middleware |
| Data status | 4 | Indicates status of data-based modules and data integrity |
| Algorithm module status | 20 | Indicates status of algorithm modules |

(5) algorithm status defined as:

| Field name | Length (bits) | Purpose |
| --- | --- | --- |
| Motion planning status | 8 | Indicates status of motion planning module |
| Control status | 8 | Indicates status of control module |
| Prediction status | 8 | Indicates status of prediction module |
| Localization/ Pose status | 8 | Indicates status of localization and pose modules |

The message formats shown above are exemplary, and other formats with different lengths for the bitfields, as well as additional bitfields and status indicators, are envisioned as part of the disclosed technology.

In some embodiments, the status messages may further include a status indicator and specific information elements. In some embodiments, the status indicators may have levels or tiers, as shown in the example table below:

| Status | Data in report |
| --- | --- |
| OK | Basic vehicle (dynamic) information; e.g. location, fuel level, engine temperature, etc. |
| Warning | Warning messages and logs |
| Error | Error logs |
| Fatal | Sensor data that may identify the fatal condition |

Figure 3:
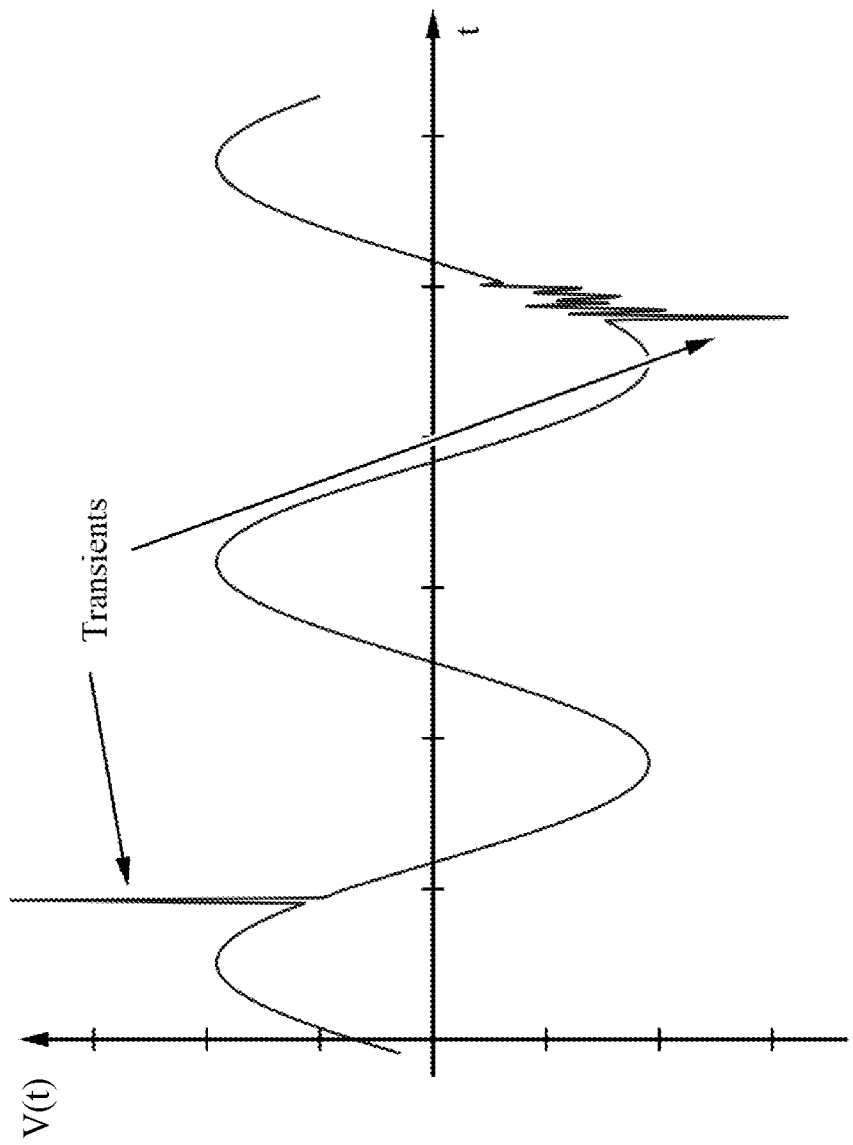
FIG. 3 shows an example of transient components in a voltage signal.

In some embodiments, the signals generated by the component may include voltage and/or current signals. In an example, erroneous operation of the component may result in voltage spikes or inrush currents in the voltage or current signals, respectively. FIG. 3 shows an example of transient components in a voltage signal.

In some embodiments, information in the messages and signals from the components is integrated to output an operational status of the component (e.g., performed by the signal analyzer 255 in FIG. 2). For an example, the presence of an error message in the messages received and a transient in the current and/or voltage signals is indicative of the operating status being faulty. In another example, the presence of a transient in the current and/or voltage signals is considered to be indicative of the operating status being faulty, despite the messages not containing an error message.

In an example, the component 200 may be a vehicle control unit (VCU), which includes a sensor power supply module (an electrical sub-component 215) and an analog digital control module (an electronic sub-component 225). The VCU may further include additional electrical and electronic sub-components that may be configured to provide signals to the signal analyzer 255 for system malfunction detection.

In another example, the component 200 may be the cooling system of a diesel or gasoline engine, which includes an engine control unit (ECU) (an electronic sub-component 225, which may be a 32-bit processor) and a temperature sensor (an electrical sub-component 215 that measures the engine temperature and outputs a scalar analog temperature).

In yet another example, the emission control system of a diesel engine may be the component 200, which includes an ECU (electronic sub-component 225) and a nitrogen oxide ($NO_x$) sensor (an electrical sub-component 215 that measures, for example, the amount of nitric oxide in the exhaust and outputs an analog scalar value).

In yet another example, the anti-lock braking system (ABS) may be the component 200, which includes an ECU (electronic sub-component 225) and a speed sensor (an electro-mechanical sub-component 215 that measures, for example, the acceleration or deceleration of the wheel of the vehicle).

In yet another example, the fuel injector may be the component 200, which includes an ECU (electronic sub-component 225) and a solenoid (an electro-mechanical sub-component 215 that generates, for example, a magnetic field to control one or more valves of the fuel injector).

Detecting transient components. Embodiments of the disclosed technology can be configured to detect transients in the voltage and/or current signals by tracking the instantaneous magnitude of the signal or by correlating the current or voltage signal with predetermined transient signal templates. In an example, transients may be caused by high-current equipment switching (e.g., an inductive load like a motor will create a kickback spike when it is turned off).

In some embodiments, the transients in the voltage and current signals can be processed using a voltage spike detection circuit that measures the instantaneous magnitude of the input voltage signal, and can determine the presence of a voltage spike by operating at a high sampling rate, e.g., up to 5 MHz sampling rate that can capture a 60-μsec impulsive transient. In another example, the sampling rate may be between 100 Hz and 1 kHz.

Transients can either be "impulsive" transients that are characterized by high-frequency spikes that protrude from the waveform, or "oscillatory" transients that are characterized by a ringing waveform that rides on or distorts the normal waveform. The latter type of transients are typically lower frequency but higher energy.

In some embodiments, different types of transients that are present in voltage and current signals (e.g., voltage spikes and inrush currents, respectively) can be stored as templates and correlated against the incoming voltage and current signal. This enables the detection of the specific transient components present in the signal, which can advantageously provide additional information that just the presence of transients.

For an example, a transient may have a characteristic pulse shape during the turning on/off or resetting of the component, which can be detected by comparing is to the stored templates, i.e., the stored templates may comprise different characteristic pulse shapes, thereby enabling their identification during operation. For another example, a transient is characterized by a rise time (due to a high-frequency component of the transient) and/or a ringing (due to a low-frequency component of the transient). In this latter case, the stored templates may comprise different combinations of rise times and ringing characteristics that advantageously enable operating transients to be identified.

Trading off error messages and transient components. As described in the context of FIG. 2, the signal analyzer 225 generates the operational status indicator of the component based on the messages (e.g., error messages in the messages) and signals (e.g., transients in the current or voltage signals) received from the electronic and electrical sub-component, respectively. In some embodiments, the signal analyzer 255 may be configured to generate the operational status indicator based on a tradeoff between the severity of the error message and the number (or periodicity) and magnitude of the transients in the signal.

For an example, if the error message has a "Fatal" status, then the operational status is deemed to be faulty irrespective of the presence or absence of transients. For another example, a "Warning" status in the error message and a few solitary transients in the voltage signal may not be flagged as indicative of faulty operation.

Comparing relationships between different signals. In some embodiments, the electric signal and a message from a related electronic component can be compared to ascertain the operational status of a component. In an example, the message may include an acceleration command from an engine of the autonomous vehicle, and the electrical signal is measurement signal of the speed. The driver or the ADS may issue an acceleration pedal command for 10 sec, which is acknowledged by the by the engine. However, if the speed measurement has not increased within an expected speed range (e.g., 3-8 miles per hour) after a predetermined amount of time (e.g., 5 seconds), then comparing the message and the electrical signal may indicate an issue with the powertrain of the vehicle.

Exemplary Embodiments of the Disclosed Technology

Figure 4:
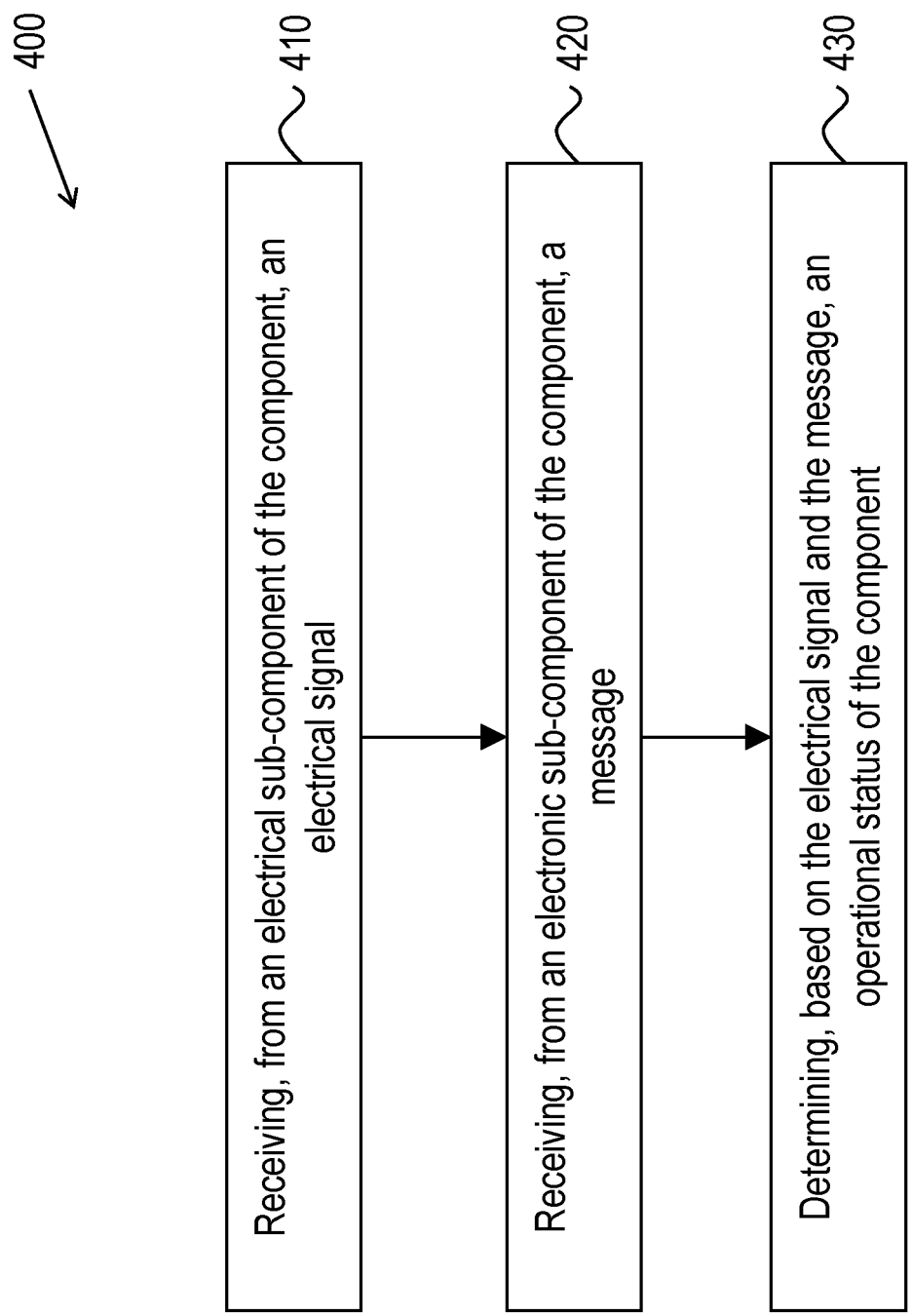
FIG. 4 shows a flowchart of an example method for using system-level malfunction indicators, in accordance with embodiments of the disclosed technology.

FIG. 4 shows a flowchart for an example method 400 for diagnosing a fault in a component of an autonomous vehicle.

The method 400 includes, at operation 410, receiving, from an electrical sub-component of the component, an electrical signal.

The method 400 includes, at operation 420, receiving, from an electronic sub-component of the component, a message.

The method 400 includes, at operation 430, determining, based on the electrical signal and the message, an operational status of the component.

In some embodiments, the message comprises an acceleration command from an engine, the electrical signal is a speed measurement, and the operational status is determined to be faulty if the speed measurement does not correspond to an expected speed measurement after a predetermined amount of time. For example, the predetermined amount of time may be 5 seconds and the expected speed measurement is in a range of 3-8 miles per hour.

In some embodiments, the electrical signal comprises a voltage signal.

In some embodiments, the method 400 further includes the operation of detecting a presence of a transient component in the voltage signal.

In some embodiments, detecting the presence of the transient component comprises correlating the voltage signal with a plurality of transient signal templates.

In some embodiments, the transient component comprises one or more voltage spikes or an overvoltage in the voltage signal.

In some embodiments, the method 400 further includes the operation of determining, based on the detecting and the message comprising an error message, the operational status to be faulty.

In some embodiments, the method 400 further includes the operation of determining, based on the detecting, the operational status to be faulty despite the message excluding an error message.

In some embodiments, the electrical signal comprises a current signal.

In some embodiments, the method 400 further includes the operation of detect a presence of a transient component in the current signal.

In some embodiments, the transient component comprises one or more indications of an inrush current in the current signal.

In some embodiments, the component of the autonomous vehicle comprises a cooling system of a gasoline or diesel engine, wherein the electronic sub-component comprises an electronic control unit (ECU) and the electrical sub-component comprises a temperature sensor configured to measure a temperature of the gasoline or diesel engine.

In some embodiments, the component of the autonomous vehicle comprises an emission control system of a diesel engine, wherein the electronic sub-component comprises an electronic control unit (ECU) and the electrical sub-component comprises a nitrogen oxide (NOx) sensor configured to measure an amount of nitric oxide in an output of the emission control system.

In some embodiments, the component of the autonomous vehicle comprises an anti-lock braking system (ABS), wherein the electronic sub-component comprises an electronic control unit (ECU) and the electrical sub-component comprises a speed sensor configured to measure an acceleration or deceleration of a wheel of the autonomous vehicle.

In some embodiments, the component of the autonomous vehicle comprises a fuel injector system, wherein the electronic sub-component comprises an electronic control unit (ECU) and the electrical sub-component comprises at least one solenoid configured to control one or more valves of the fuel injector system.

In some embodiments, the method 400 further includes the operation of detecting a presence of a transient component in the electrical signal based on correlating the electrical signal with a plurality of transient signal templates, wherein each of the plurality of transient signal templates comprises a distinct rise time.

In some embodiments, each of the plurality of transient signal templates further comprises a distinct ringing characteristic.

In some embodiments, detecting the presence of the transient component is based on continuous monitoring of the electrical signal.

Figure 5:
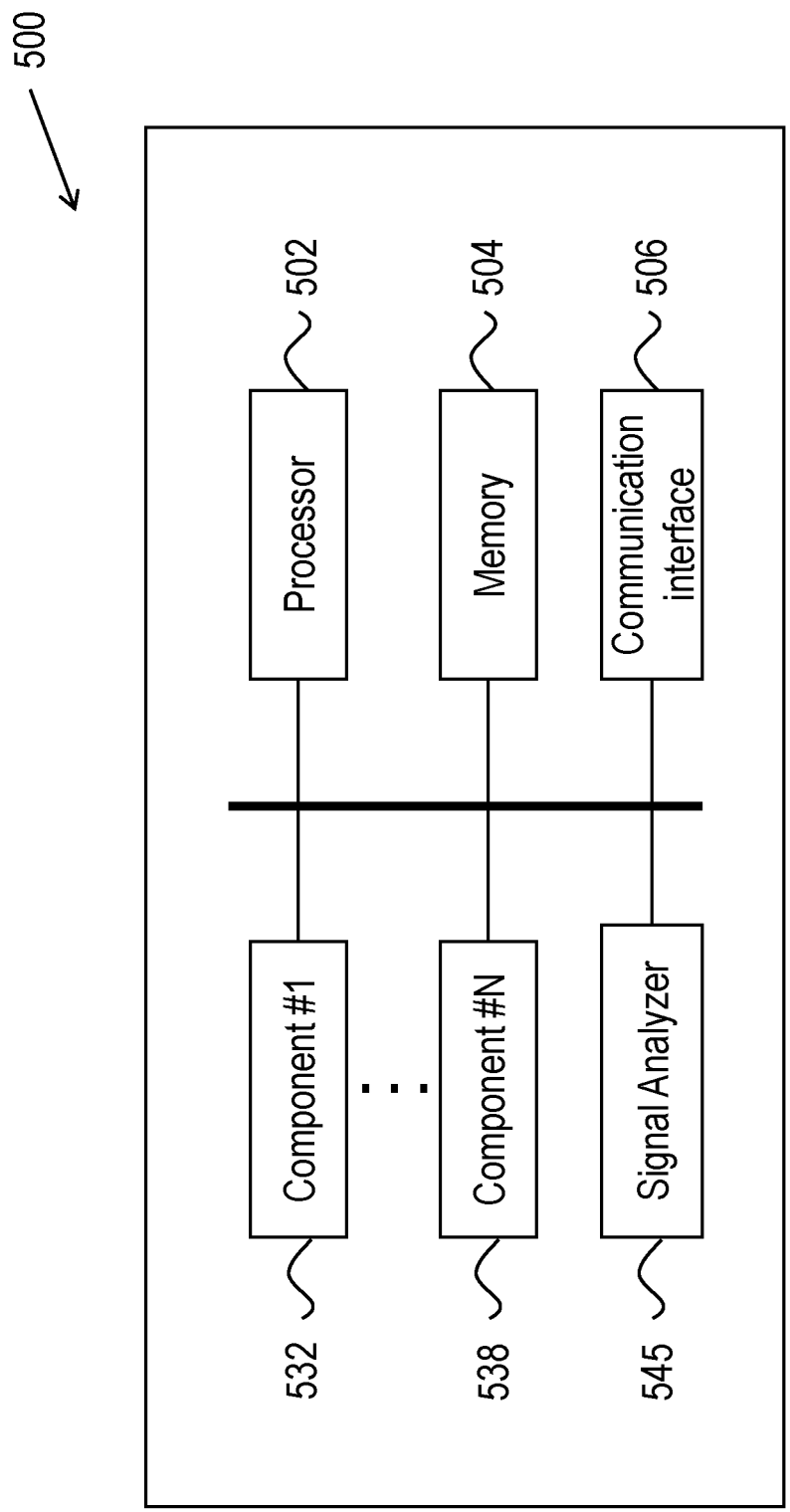
FIG. 5 shows an example of a hardware platform that can implement some techniques described in the present document.

FIG. 5 shows an example of a hardware platform 500 that can be used to implement some of the techniques described in the present document. For example, the hardware platform 500 may implement the method 400 or may implement the various modules described herein. The hardware platform 500 may include a processor 502 that can execute code to implement a method. The hardware platform 500 may include a memory 504 that may be used to store processor-executable code and/or store data. The hardware platform 500 may further include a communication interface 506. For example, the communication interface 506 may implement one or more of the communication protocols (LTE, Wi-Fi, and so on) described herein. The hardware platform may further include multiple components (denoted Component #1 532 to Component #N 538) and a signal analyzer 545. In some embodiments, some portion or all of the signal analyzer 545 may be implemented in the processor 502.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, e.g., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A fault diagnostic method, comprising:
receiving an electrical signal from a first component located in a vehicle, wherein the electrical signal includes a transient signal of a voltage signal or a current signal of the electrical signal;
receiving a first message from a second component located in the vehicle, wherein the first message includes an error message; and
determining an operational status of a third component that includes the first component and the second component, wherein the operational status is determined based on the transient signal of the voltage signal or the current signal and based on the error message in the first message,
wherein the operational status of the third component is determined based on a tradeoff between a severity of the error message and a plurality of characteristics of the transient signal of the voltage signal or the current signal, and
wherein the plurality of characteristics of the transient signal includes a number of transients of the transient signal and magnitude of the transient signal.

2. The fault diagnostic method of claim 1, wherein the plurality of characteristics of the transient signal includes a periodicity of the transient signal.

3. The fault diagnostic method of claim 1, wherein the operational status is determined to be faulty in response to the error message including a fatal status indicating a fatal condition irrespective of a presence of the transient signal.

4. The fault diagnostic method of claim 1, wherein the operational status is determined to not be faulty in response to the error message including a warning status and in response to the transient signal including solitary transients.

5. The fault diagnostic method of claim 1, wherein the first message includes a vehicle status message that includes a first field that indicates whether the vehicle is running or has stopped using one-bit.

6. A fault diagnostic apparatus, comprising:
a processor; and
a memory with instructions thereon, wherein the instructions upon execution by the processor cause the processor to:
receive an electrical signal from a first component located in a vehicle, wherein the electrical signal includes a transient signal of a voltage signal or a current signal of the electrical signal;
receive a first message from a second component located in the vehicle, wherein the first message includes an error message; and
determine an operational status of a third component that includes the first component and the second component, wherein the operational status is determined based on the transient signal of the voltage signal or the current signal and based on the error message in the first message,
wherein the operational status of the third component is determined based on a tradeoff between a severity of the error message and a plurality of characteristics of the transient signal of the voltage signal or the current signal, and
wherein the plurality of characteristics of the transient signal includes a number of transients of the transient signal and magnitude of the transient signal.

7. The fault diagnostic apparatus of claim 6, wherein the plurality of characteristics of the transient signal includes a periodicity of the transient signal.

8. The fault diagnostic apparatus of claim 6, wherein the operational status is determined to be faulty in response to the error message including a fatal status indicating a fatal condition irrespective of a presence of the transient signal.

9. The fault diagnostic apparatus of claim 6, wherein the operational status is determined to not be faulty in response to the error message including a warning status and in response to the transient signal including solitary transients.

10. The fault diagnostic apparatus of claim 6, wherein the first message includes a vehicle status message that includes a first field that indicates whether the vehicle is running or has stopped using one-bit.

11. A non-transitory computer readable storage medium having instructions stored thereupon, the instructions, when executed by a processor, causing the processor to implement a method, the method comprising:
receiving an electrical signal from a first component located in a vehicle, wherein the electrical signal includes a transient signal of a voltage signal or a current signal of the electrical signal;
receiving a first message from a second component located in the vehicle, wherein the first message includes an error message; and
determining an operational status of a third component that includes the first component and the second component, wherein the operational status is determined based on the transient signal of the voltage signal or the current signal and based on the error message in the first message,
wherein the operational status of the third component is determined based on a tradeoff between a severity of the error message and a plurality of characteristics of the transient signal of the voltage signal or the current signal, and
wherein the plurality of characteristics of the transient signal includes a number of transients of the transient signal and magnitude of the transient signal.

12. The non-transitory computer readable storage medium of claim 11, wherein the plurality of characteristics of the transient signal includes a periodicity of the transient signal.

13. The non-transitory computer readable storage medium of claim 11, wherein the operational status is determined to be faulty in response to the error message including a fatal status indicating a fatal condition irrespective of a presence of the transient signal.

14. The non-transitory computer readable storage medium of claim 11, wherein the operational status is determined to not be faulty in response to the error message including a warning status and in response to the transient signal including solitary transients.

15. The non-transitory computer readable storage medium of claim 11, wherein the first message includes a vehicle status message that includes a first field that indicates whether the vehicle is running or has stopped using one-bit.

* * * * *